United States Patent
Espina Perez

(10) Patent No.: US 8,884,754 B2
(45) Date of Patent: Nov. 11, 2014

(54) MONITORING VITAL PARAMETERS OF A PATIENT USING A BODY SENSOR NETWORK

(75) Inventor: Javier Espina Perez, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 714 days.

(21) Appl. No.: 13/059,234

(22) PCT Filed: Aug. 18, 2009

(86) PCT No.: PCT/IB2009/053641
§ 371 (c)(1),
(2), (4) Date: Feb. 16, 2011

(87) PCT Pub. No.: WO2010/020945
PCT Pub. Date: Feb. 25, 2010

(65) Prior Publication Data
US 2011/0137133 A1    Jun. 9, 2011

(30) Foreign Application Priority Data

Aug. 20, 2008  (EP) .................................... 08105082

(51) Int. Cl.
| | |
|---|---|
| *G08B 1/08* | (2006.01) |
| *H04W 40/12* | (2009.01) |
| *G06F 19/00* | (2011.01) |
| *A61B 5/00* | (2006.01) |

(52) U.S. Cl.
CPC ........... *H04W 40/12* (2013.01); *G06F 19/3418* (2013.01); *A61B 5/002* (2013.01); *A61B 5/0024* (2013.01)

USPC ............. 340/539.13; 340/539.12; 340/539.11

(58) Field of Classification Search
USPC .................................. 340/531–539.32; 705/3
See application file for complete search history.

(56) References Cited

U.S. PATENT DOCUMENTS

| | | | |
|---|---|---|---|
| 2005/0275532 | A1 | 12/2005 | Ferri et al. |
| 2006/0002368 | A1* | 1/2006 | Budampati et al. ........... 370/351 |
| 2007/0088225 | A1 | 4/2007 | Tanaka et al. |
| 2007/0242642 | A1 | 10/2007 | Bronez |
| 2007/0299480 | A1 | 12/2007 | Hill |
| 2008/0001735 | A1* | 1/2008 | Tran ........................ 340/539.22 |
| 2008/0094226 | A1 | 4/2008 | O'Shea et al. |
| 2008/0129465 | A1* | 6/2008 | Rao .......................... 340/286.02 |
| 2008/0219202 | A1* | 9/2008 | Pandey et al. .................. 370/315 |
| 2009/0058636 | A1* | 3/2009 | Gaskill et al. ............ 340/539.11 |

FOREIGN PATENT DOCUMENTS

| | | | |
|---|---|---|---|
| CN | 101083658 | * | 12/2007 |
| CN | 101083658 | A | 12/2007 |

(Continued)

*Primary Examiner* — Mohammad Ghayour
*Assistant Examiner* — Jerold Murphy

(57) ABSTRACT

The invention relates to a method of monitoring a plurality of vital parameters of a patient 10 using a body sensor network with a set of on-body sensors 1 and at least one off-body monitoring device 2, the method comprising the following steps: with each on-body sensor 1, sensing a vital parameter and transmitting data related to the sensed vital parameter to the off-body monitoring device 2, and for at least one of the on-body sensors 1, determining the inclination of this on-body sensor 1 relative to the off-body monitoring device 2. In this way, a reliable and easy to use possibility for monitoring vital parameters of a patient 10 using a body sensor network is provided that minimizes the performance problem produced by RF attenuation caused by the body of the patient 10.

9 Claims, 2 Drawing Sheets

(56) References Cited

FOREIGN PATENT DOCUMENTS

| | | | |
|---|---|---|---|
| JP | 2006263002 A | 10/2006 |
| WO | 2006111948 A2 | 10/2006 |
| WO | 200796810 A1 | 8/2007 |
| WO | 2008018810 A2 | 2/2008 |
| WO | 2008097524 A2 | 8/2008 |

* cited by examiner

MONITORING VITAL PARAMETERS OF A PATIENT USING A BODY SENSOR NETWORK

FIELD OF THE INVENTION

The invention relates to the field of monitoring vital parameters of a patient using a body sensor network, and especially to improving data transmission between on-body sensors of a body sensor network with an off-body monitoring device.

BACKGROUND OF THE INVENTION

A body sensor network (BSN) is a network of devices that communicate wirelessly with one another and are located in the body or on the body of a person like a patient, or in the immediate vicinity of the body. Due to the convenience enabled by the absence of cables, BSNs are increasingly being used for patient monitoring as well as for many other applications. A typical BSN, as used for patient monitoring, consists of a set of on-body sensors and one off-body monitoring device that receives the vital sign data measured and transmitted by the sensors. The monitoring device is usually located within a distance of less than five meters from the patient's body.

It is preferred that patient monitoring BSNs communicate at frequencies higher than 2 GHz because those frequency bands are especially suitable in terms of licensing costs, data transmission rate and antenna size. Nevertheless, the high attenuation introduced by the human body at frequencies above 1 GHz is the main challenge for reliable BSNs. Since high RF frequencies barely propagate through the body, parts of the person's body often block out the direct RF propagation path—i.e. the visibility or line-of-sight (LOS)—between BSN devices. Although two devices without LOS can often communicate, the non-LOS link between them is much less reliable than a LOS link.

Wireless communication via non-LOS is still possible because of two effects: multipath propagation and creeping waves. Thanks to multipath propagation a device without LOS receives multiple reflections of the signal transmitted by another device. Such reflections originate when the transmitted RF signal bounces off the user's environment, e.g. floor, walls, furniture, etc., and hence heavily depend on it. The creeping waves effect can be understood as a diffraction or waveguide effect that causes the RF signal of a device to propagate following the contour of the body. Both multipath propagation and the creeping waves help on-body BSN devices to communicate. Nonetheless off-body devices such as a patient monitor cannot benefit from the creeping waves and depend solely on the reflections from the environment.

As set out above, conventional body sensor networks, also known as body area networks (BANs), are not reliable enough for health monitoring, mainly due to the poor RF propagation conditions introduced by the proximity of the human body. Although the attenuation problem is especially detrimental for medical BSNs it has also been identified in other kinds of networks and for other application domains. Most conventional approaches to address this problem are reactive approaches based on first monitoring the conditions on the wireless link using packet or bit error rates (PER and BER), received signal strength, or other signal quality metrics, and, then, performing countermeasures whenever the link conditions become adverse. Such countermeasures include the following:

A first conventional approach is to use an alternative link that was assessed to have better conditions to deliver data. Thus a device sends its data to an intermediary device instead of to the destination device. Most packet routing protocols are based on this. Further, another conventional approach is increasing the transmit power to ensure a better signal at the receiving device. This is known as dynamic link adaptation, dynamic power management, or dynamic link power control. A further conventional possibility is decreasing the data rate with which information is physically transmitted in order to decrease the transmission error probability. For example, this mechanism is used in wireless technologies, and for example referred to as dynamic rate scaling.

Other approaches apply precautionary measures independently of the actual conditions of the wireless link. Some of the most relevant are the following:

Antennas optimized for on-body operation can be used in order to reduce the magnitude of the attenuation. Further, the transmit power can be increased permanently in order to ensure a better signal at the receiving device. Furthermore, using flooding-based packet routing so that every device forwards the packets received from all its neighboring devices is another conventional possibility. Since the same information is sent via multiple routes in parallel, it is more probable that it arrives at its destination.

However, the conventional state-of-the-art approaches to tackle the RF attenuation issues are only partially successful and exhibit important disadvantages. For instance, the first three approaches mentioned before cannot completely prevent the loss of information because they are based on reactive measures and cannot anticipate a degradation of the link conditions. In other words: They typically react to a problem when it has already occurred. Precautionary approaches are not much more successful: While the fourth approach mentioned above enables only a minimal improvement of the wireless link conditions, the fifth approach dramatically reduces the operating time of the BSN and the sixth approach quickly overloads the wireless channel.

SUMMARY OF THE INVENTION

It is the object of the invention to provide a reliable and easy to use possibility for monitoring vital parameters of a patient using a body sensor network that minimizes the BSN performance problem produced by the RF attenuation caused by the body of the patient.

This object is achieved by a method of monitoring a plurality of vital parameters of a patient using a body sensor network with a set of on-body sensors and at least one off-body monitoring device, the method comprising the following steps:

with each on-body sensor, sensing a vital parameter and transmitting data related to the sensed vital parameter to the off-body monitoring device, and for at least one of the on-body sensors, determining the inclination of this on-body sensor relative to the off-body monitoring device.

Accordingly, it is an essential idea of the invention that for at least one of the on-body sensors the inclination of the sensor is determined and, thus, the posture of the patient's body or a patient's limb can be detected. This provides for the possibility of using different data delivery routes than the direct data delivery route from one on-body sensor to the off-body monitoring device as set out in detail further below.

It should be noted that the term "patient" used here is to be understood to mean any human being or animal, that uses a body sensor network, i.e. that carries on-body sensors that communicate with an off-body monitoring device, no matter if the human being or animal is healthy or diseased.

As already stated further above, the on-body sensors are preferably provided on or in the body of the patient or in its immediate vicinity. Further, as for conventional body sensor networks, it is preferred that the on-body sensors do not only transmit data to the off-body monitoring device but are also able to share data with each other, i.e. transmit data from on-body sensor to another on-body sensor.

Further, it is preferred that all of the on-body sensors of a body sensor network have transmitting capabilities for transmitting data to the off-monitoring device. However, it is also possible that further on-body sensors are provided which do not have such direct transmitting capability, i.e. which always use another on-body sensor for transmitting data to the off-body monitoring device. However, such on-body sensors without direct transmitting capability will not be discussed in the following, though they might be part of a body sensor network for which the method according to the invention is used.

According to a preferred embodiment of the invention, the method further comprises the step of determining the on-body location of at least one on-body sensor. With respect to that, it is especially preferred that the on-body location is determined for such an on-body sensor for which also the inclination is determined. Further, it is especially preferred that the inclination and the on-body location are determined for a plurality of on-body sensors, most preferably for all on-body sensors.

Further, according to a preferred embodiment of the invention, the method comprises a step of determining the quality of the direct data delivery route between at least one on-body sensor for which the inclination and the on-body location has been determined and the off-monitoring device, wherein the quality is calculated on the basis of the inclination and the on-body location of the on-body sensor. With respect to this, as "direct data delivery route" such a route is meant which provides for the possibility of directly transmitting data from the respective on-body sensor to the off-body monitoring device without requiring another on-body sensor as an intermediate station. Moreover, with respect to determining the quality of the direct data delivery route, it is especially preferred to classify the quality in one of a plurality of quality classes. For example, it is possible to classify the quality of the direct data delivery route as "reliable", "medium" or "unreliable".

According to another preferred embodiment of the invention, the method further comprises the step of deciding to route the data of a first on-body sensor via another on-body sensor to the off-body monitoring device if the quality of the direct data delivery route between the first on-body sensor and the off-body monitoring device is less than a predefined value. Referring to the example given above, if the quality of the direct data delivery route between the on-body sensor and the off-body monitoring device is classified to be "unreliable", this route is not used anymore and instead it is decided to use another on-body sensor as intermediate station for data transmittance to the off-body monitoring device.

For deciding which other on-body sensor to use for above-mentioned case, according to a preferred embodiment of the invention, the method further comprises the step of routing the data of the first on-body sensor via a second on-body sensor to the off-body monitoring device, the quality of the second on-body sensor being better than the quality of the first on-body sensor. As an example, it can be decided that the quality of the second on-body sensor has to be at least classified to be "medium" in order to be used.

Furthermore, according to another preferred embodiment of the invention, the method further comprises the step of choosing the second on-body sensor out of the set of other on-body sensors based on the expected remaining operating time of the other on-body sensors, respectively. This means for example that in case of battery driven on-body sensors, which is preferred, a longer total runtime of the body sensor network can be achieved if such on-body sensors are used as intermediate stations which have longer expected remaining operating times because of their remaining battery power.

According to another preferred embodiment of the invention, the method further comprises the step of choosing the second on-body sensor out of the set of other on-body sensors based on the number of hops, i.e. links, of the respective data delivery route via the respective other on-body sensors. This measure is preferred since routes with a lesser number of links, i.e. hops, improve a reliability of the respective route, minimizing the overall power consumption and reducing data delivery latency.

Furthermore, according to a preferred embodiment of the invention, the method comprises the step of monitoring and storing the performance of at least two different data delivery routes in relation to the patient's posture detected by inclination of an on-body sensor. Further, with respect to this, it is preferred that the method comprises the step of choosing the second on-body sensor out of the set of other on-body sensors based on the stored performance of a respective data delivery route comprising the respective other on-body sensor. For this case, the performance of data delivery routes can be determined in different ways, e.g. based on packet error rates.

Further, above-mentioned method is also addressed by a body sensor network for monitoring a plurality of vital parameters of a patient, with
  a set of on-body sensors and at least one off-body monitoring device, wherein
  the on-body sensors are each adapted for sensing a vital parameter and for transmitting data related to the sensed vital parameter to the off-body monitoring device, and wherein
  at least one of the on-body sensors comprises an inclination sensor.

Accordingly, the body sensor network according to the invention relates to the method for monitoring vital parameters of a patient as described above, wherein for determining the inclination of an on-body sensor this on-body sensor comprises an inclination sensor. As already stated above, there may be further on-body sensors which do not transmit their data directly to the off-body monitoring device but via another on-body sensor. Such sensors, though they may be present, will not be discussed in the following.

In general, there are different possibilities for the inclination sensor. However, according to a preferred embodiment of the invention, the inclination sensor comprises an accelerometer, a gyrometer or/and an magnetometer. All these devices for sensing the inclination can be manufactured as micro devices and, thus, can easily be integrated into the on-body sensor.

Further, according to a preferred embodiment of the invention, at least one of the on-body sensors comprises a storage device in which its on-body location is stored. In this way, the on-body location of a respective on-body sensor can be determined in an easy and reliable way.

Furthermore, according to a preferred embodiment of the invention, a communication frequency for the wireless communication between the on-body sensors and the off-body communication device of $\geq 2$ GHz is provided. As set out further above, this frequency range is preferred since it is suitable in terms of licensing costs, data transmission rate and antenna size, the latter been especially relevant for such on-body sensors which are convenient to wear.

As a result, the invention provides for a possibility for minimizing the BSN performance problem produced by the RF attenuation caused by the body of the patient without the important disadvantages of other approaches, such as the reactive and precautionary approaches described further above. According to a preferred embodiment of the invention, this is achieved by means of a predictive approach that consists in routing the data of a BSN device via another BSN device based on the patient's posture and the on-body location of both devices. In this case, the route of device data is therefore not determined as a result of an assessment of the quality of the wireless links between a device and other nearby devices but rather as a result of the devices' locations on the body and their inclinations, which are strongly related to the body posture. Such metric unveils the susceptibility of wireless links to sudden communication failures and empowers the BSN to decide which links are most reliable before any deterioration occurs.

The on-body location information is preferably inferred from the functionality description contained in the BSN devices, e.g. chest-ECG sensor or ear-SpO2 sensor. In most practical cases the functionality of a BSN device reveals the spot of the body on which it is worn. The inclination information is preferably derived using existing algorithms that process the output signal of an inclination sensor which is preferably built in the BSN devices.

The proposed solution uses inclination information derived locally on the BSN devices, i.e. the sensors. For that, these devices preferably comprise inclination-sensitive hardware, e.g. a 3D accelerometer chip, and inclination calculation software. Such sensors have proven to be feasible in terms of size, processing power and power consumption.

The invention provides for the possibility of improving the reliability of BSNs and makes their performance less dependent on the RF attenuation caused by postures changes. Thus, the most important problem of BSNs is herewith addressed. As opposed to other existing approaches the invention avoids communication failures before they occur. Further, the invention can be used simultaneously to other approaches such as packet retransmissions, dynamic link adaptation or others.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
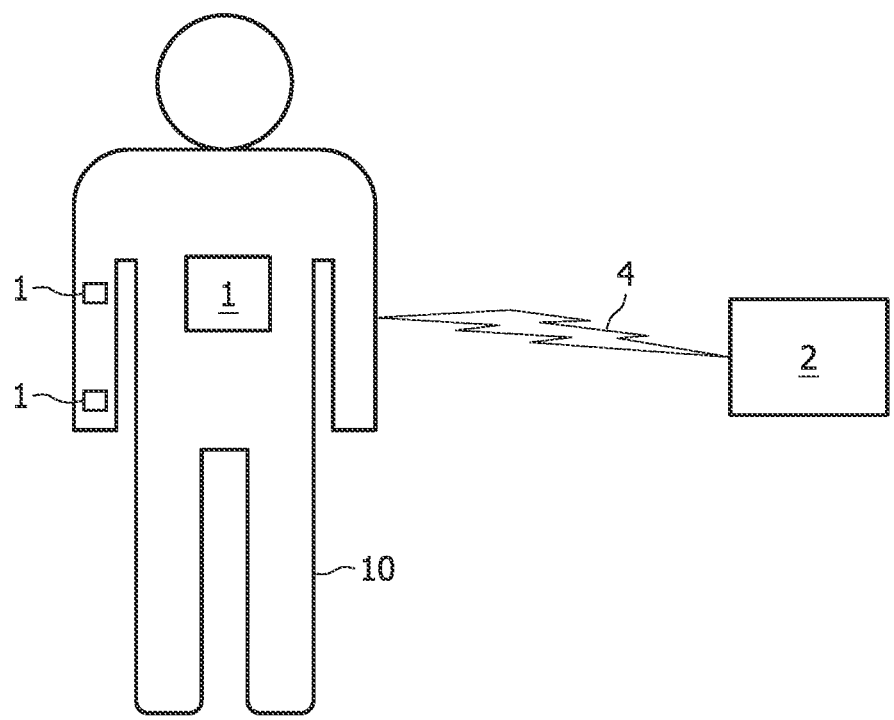
FIG. 1 shows a schematic depiction of a body sensor network for monitoring vital parameters of a patient according to an embodiment of the invention.

From FIG. 1 a body sensor network for monitoring a plurality of vital parameters of a patient 10 according to an embodiment of the invention can be seen. This network comprises a set of on-body sensors 1 which are worn by the patient 10, and an off-body monitoring device 2, wherein the on-body sensors 1 are each adapted for sensing a vital parameter, like an ECG signal or a blood pressure signal, and for transmitting data related to the respective vital parameter to the off-body monitoring device 2 via a wireless connection 4.

Figure 2:
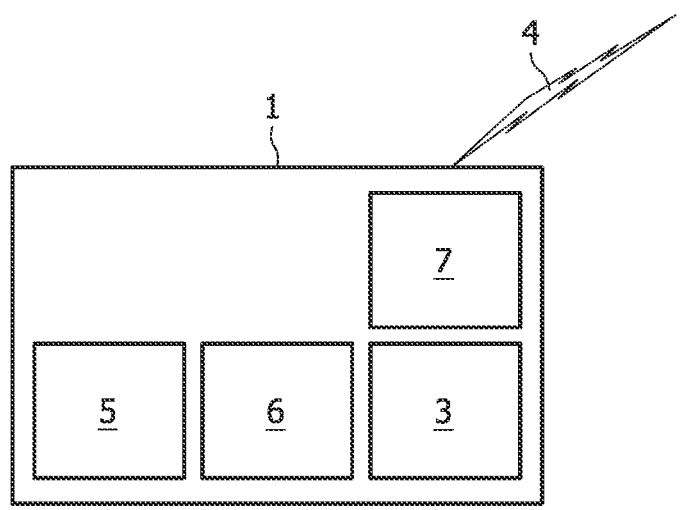
FIG. 2 schematically shows an on-body sensor of such a body sensor network in more detail.

Further, as can be seen from FIG. 2, the on-body sensors 1 each comprise a sensing unit 5 for actually sensing the vital parameter, and an inclination sensor 3 which preferably is an accelerometer, a gyrometer or/and a magnetometer. Furthermore, the on-body sensors 1 each comprise a storage device 6 in which its respective on-body location is stored, i.e. "chest" for an ECG sensor. The on-body sensors 1 also each comprise a transmitter/receiver unit 7 for transmitting data to the off-body monitoring device 2 or to another on-body sensor 1, and for receiving data from another on-body sensor 1.

According to this embodiment of the invention, on the basis of the inclination and the on-body location of each of the on-body sensors 1, the quality of the direct data delivery route between each of the on-body sensors 1 and the off-body monitoring device 2 is calculated. In this way, without actually sending data over the respective routes, the quality of each direct data delivery route is determined and classified as being "reliable", "medium" or "unreliable". If the quality of the direct data delivery route between an on-body sensor 1 and the off-body monitoring device 2 is determined to be less than a predefined value, e.g. is not determined to be at least "medium", according to the embodiment of the invention, it is decided to route the data of the on-body sensor 1 with the insufficient direct data delivery route via another on-body sensor 1 with a better quality of the direct data delivery route to the off-body monitoring device 2.

Accordingly, on-body sensors 1 of the BSN according to the preferred embodiment of the invention are capable of knowing their on-body location and their inclination. As mentioned before, the on-body sensors 1 preferably deduce their location from their locally available functionality information, e.g. "chest" for ECG, "finger" for SpO2, . . . , which is stored in the respective storage device 6 of the on-body sensor 1. Moreover, the on-body sensors 1 interpret the signal of their local inclination-sensitive hardware, e.g. the accelerometer, gyrometer, or magnetometer, in order to obtain their inclination, which reveals to which extent the body should be blocking the LOS of their different wireless links.

According to the embodiment of the invention described here, the on-body sensors 1 feature a small low-power 3D accelerometer chip as an inclination sensor 3 that allows them to obtain their inclination with respect to the ground and therefore to the off-body monitoring device 2, provided the inclination of the latter with respect to the ground is known. The DC components of the 3 acceleration signals, which contain information of the accelerometer's inclination with respect to the ground are analyzed. Since gravity creates a constant acceleration towards ground, its projection on the 3 axis of the accelerometer unveils the inclination of those axis and, hence, of the respective on-body sensors 1. In this way, when the patient 10 is lying on his back, a chest-worn on-body sensors 1 will detect that it is facing up. On the other hand, if the patient 10 turns in bed and lays on his chest, the same on-body sensors 1 will detect that it is facing down. For a correct inclination calculation it is preferred to calibrate the on-body sensors 1 during the BSN set-up, which may be done requiring patient action, e.g. pressing a button, while the patient holds a predefined posture, e.g. standing up.

Figure 3:
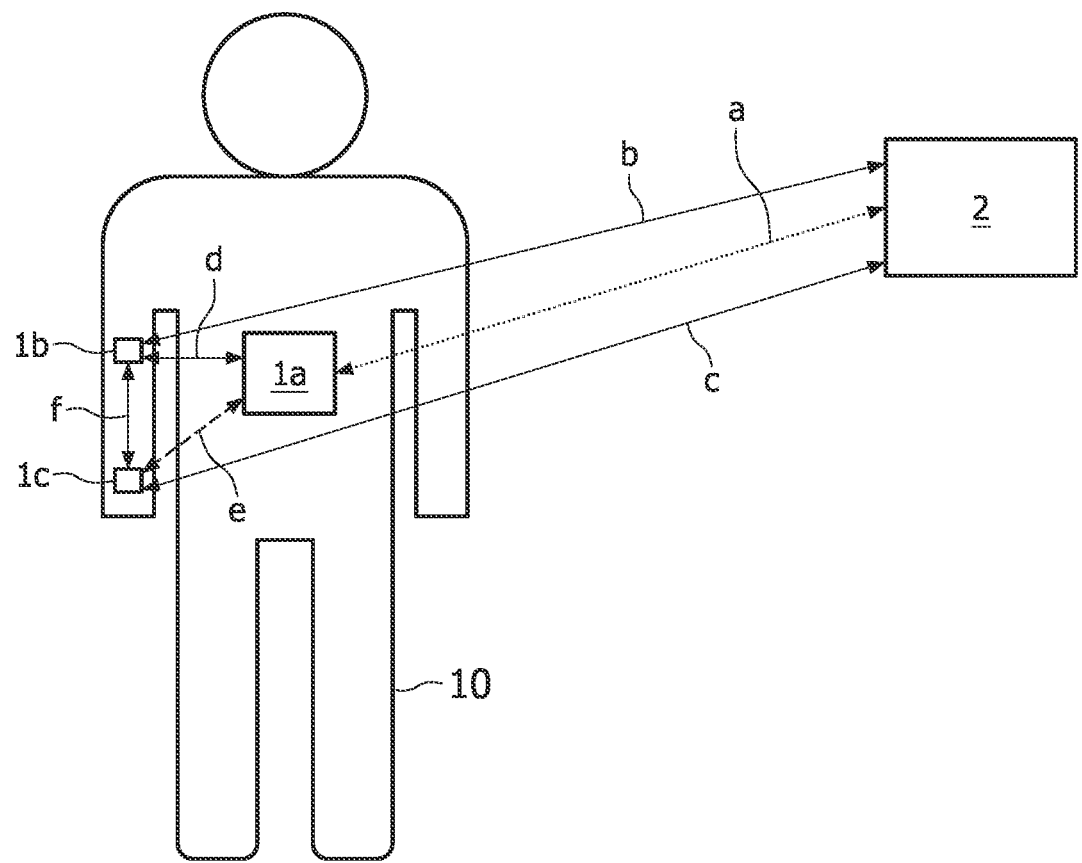
FIG. 3 schematically shows a 3-class link classification system according to an embodiment of the invention, for a patient who is lying on his chest in a bed.

The on-body sensors 1 share their location and inclination information with one another. This enables them to better estimate the patient's posture and provides them with information about the number of alternative data delivery routes within the BSN and their susceptibility to communication failures. FIG. 3 shows above mentioned 3-class classification system in which links are classified as "reliable" (full line), "medium" (dashed line), or "unreliable" (dotted line) for a patient 10 who is lying on his chest in a bed 8 according to the following:

Link a: On-body sensor 1a detects it is a chest-worn device and it is facing down. Hence, it is detected that the patient 10 is lying on his chest, which makes all off-body links starting from on-body sensor 1a, i.e. link a unreliable. Thanks to the creeping waves effect, the on-body links starting from on-body sensor 1a, i.e. link d and link e to on-body sensors 1b and 1c, respectively, are less affected by the current body posture than link a.

Link b and Link c: Both on-body sensor 1b and on-body sensor 1c detect they are arm worn. At that location body coverage by the arm is not considered to be detrimental enough, independently of the on-body sensors' 1b, 1c inclination. Therefore both on-body sensors rate their off-body links, i.e. link b and link c, as reliable.

Link d: on-body sensor 1a detects that on-body sensor 1b is a device that is located at the upper arm. Due to the proximity between the chest and the upper arm in any posture, on-body sensor 1a considers that the creeping waves are enough to maintain a reliable link and therefore rates link d as reliable, independently of the inclination of on-body sensor 1b.

Link e: On-body sensor 1a detects that on-body sensor 1c is a device that is located at the wrist. Due to the mobility of the wrist across different postures, on-body sensor 1a considers that the creeping waves might be enough to maintain a reliable link and therefore rates link e as medium, independently of the inclination of on-body sensor 1c.

Link f: On-body sensor 1b and on-body sensor 1c detect that they are both arm worn devices. Owing to their proximity and limited coverage by the arm, i.e. since it is unlikely that the user is lying with an arm under his trunk, link f is rated as reliable.

Given the aforementioned link classification, on-body sensor 1b and on-body sensor 1c decide to send their data directly to the off-body monitoring device 2. Since link d and link b are considered to be reliable, on-body sensor 1a decides to send its data via on-body sensor 1b. Hence, the on-body sensors 1a, 1b, 1c decide to change the device to which they send their data based mainly on the rating of all the links that are part of an alternative route.

In case that two or more alternative routes with the same link ratings are found, a device may choose one of them randomly or using optional additional metrics such as:

Expected remaining operating time or, equivalently, the remaining battery charge of the devices involved in a data route. Devices with a longer remaining operating time shall be preferably chosen to forward others devices' data. For that, the respective devices preferably monitor their battery load and/or power consumption profile.

Minimal number of hops which means that routes with a lesser number of links, i.e. hops, shall be preferred. A low number of hops improves the reliability of a route, minimizes overall power consumption, and reduces data delivery latency.

Performance history which means that the decision between similar alternative routes may be taken on the basis of the performance history of all BSN links in relation with the patient's posture. This is preferred when BSN devices monitor and store the performance of their different links, e.g. base on the packet error rate.

The effectiveness of the invention in minimizing body attenuation problems can be enhanced with accurate ranging or/and positioning information. Centimeter-scale ranging or/and positioning may be available when the BSN uses an UWB (Ultra Wide Band) technology for wireless data transmission. According to this embodiment, a device that detects that the off-body monitoring device, e.g. a bedside patient monitor, is very near may decide to send its data directly to the off-body monitoring device disregarding posture-based routing as described above. Although patient monitors are generally at least 50 cm to 100 cm far from the patient's body, this distance may become a few centimeters if the patient monitor is attached to the patient or his bed during patient transportation. Accurate ranging or/and positioning information may also refine the failure susceptibility classification of on-body links and therefore allow the choice of the most optimal route.

The posture-dependent routing described herewith is preferably implemented as a software component that may be called "routing manager". Depending on the communication stack layer in which the routing manager is implemented, the following implementation options are preferred:

With respect to this, one embodiment is "application level implementation": The Routing Manager is implemented as an application on top of the communication stack. It interfaces with other local applications to discover the type of device, i.e. its placement on the body, and its inclination with respect to the ground. The same information is also retrieved about other BSN devices from their remote applications. Finally, the routing manager also interfaces, directly or via a management tool, with the networking (NWK) layer for which it manages its routing table.

Another embodiment is "cross layer implementation": In this case, the routing manager is implemented within the networking (NWK) layer, the main task of which is to deal with data routing. Like the former implementation, this one also uses information that is available at the application layer of the local device and the remote devices. Since the route manager needs information from other stack layers to function, this implementation is named cross-layer.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method of monitoring vital sign data of a patient using a body sensor network with a set of on-body vital sign sensors and at least one off-body monitoring device, the method comprising the following steps:

with each on-body sensor, sensing a vital sign of the patient and transmitting vital sign data indicative of the sensed vital sign of the patient to the off-body monitoring device, wherein the on-body sensors communicate wirelessly with the off-body monitoring device and with one another, wherein at least one of the on-body sensors determines an inclination of the at least one on-body sensor relative to the off-body monitoring device, wherein the at least one on-body sensor determines the on-body location of the at least one on-body sensor, wherein the at least one on-body sensor determines a direct data delivery route between at least one on-body sensor for which the inclination and the on-body location has been determined and the off-body monitoring device, determining a reliability value indicative of data packet error rates along a direct data delivery route on the basis of the inclination and the on-body location of the at least one on-body sensor, and routing the vital sign data of the at least one on-body sensor via another on-body sensor to the off-body monitoring device if the reliability value of the direct data delivery route between the at least one on-body sensor and the off-body monitoring device is less than a predefined value.

2. The method according to claim 1, wherein the step of routing the vital sign data of the at least one on-body sensor via another on-body sensor to the off-body monitoring device is responsive to the reliability value of the direct data delivery route via of the another on-body sensor being better than the reliability value of the direct data delivery route of the at least one on-body sensor.

3. The method according to claim 1, further comprising the step of choosing the another on-body sensor out of the set of other on-body sensors based on an expected remaining operating time of the other on-body sensors, respectively.

4. The method according to claim 1, further comprising the step of choosing the another on-body sensor out of the set of other on-body sensors based on the number of hops of the respective data delivery route via the respective other on-body sensors.

5. The method according to claim 1, further comprising the step of monitoring the packet error rates and storing the reliability value of at least two different direct data delivery routes in relation to the patient's posture detected by the inclination of an on-body sensor.

6. The method according to claim 1, further comprising the step of choosing the another on-body sensor out of the set of other on-body sensors based on a stored performance of a respective data delivery route comprising the respective another on-body sensor.

7. A body sensor network for monitoring vital signs of a patient, with a set of on-body sensors and at least one off-body monitoring device, wherein the on-body sensors are each adapted for sensing a vital sign and for transmitting vital sign data related to the sensed vital sign to the off-body monitoring device, and wherein the on-body sensors communicate wirelessly with the off-body monitoring device and with each other, and wherein at least one of the on-body sensors comprises an inclination sensor configured to determine an inclination of said on-body sensor relative to the off-body monitoring device and a storage device in which an on-body location of the at least one on-body sensor is stored, and wherein the at least one on-body sensor is adapted to determine a direct data delivery route between at least one on-body sensor for which the inclination and the on-body location has been determined and the off-body monitoring device and is adapted to determine a reliability value indicative of data packet error rates along a direct data delivery route on the basis of the inclination and the on-body location of the at least one on-body sensor, wherein the at least one on-body sensor is adapted to route the vital sign data of the at least one on-body sensor via another on-body sensor to the off-body monitoring device if the reliability value of the direct data delivery route between the at least one on-body sensor and the off-body monitoring device is less than a predefined value.

8. The body sensor network according to claim 7, wherein the inclination sensor comprises an accelerometer, a gyrometer or/and a magnetometer.

9. The body sensor network according to claim 7, wherein a communication frequency for the wireless connection between the on-body sensors and the off-body monitoring device is ≥2 GHz.

* * * * *